United States Patent [19]

Müller et al.

[11] 4,327,000
[45] Apr. 27, 1982

[54] STABILIZER MIXTURES FOR STABILIZING CHLORINATED THERMOPLASTICS

[75] Inventors: Horst Müller, Fürth; Hermann O. Wirth, Bensheim, both of Fed. Rep. of Germany

[73] Assignee: Ciba-Geigy Corporation, Ardsley, N.Y.

[21] Appl. No.: 133,160

[22] Filed: Mar. 24, 1980

[30] Foreign Application Priority Data

Apr. 5, 1979 [CH] Switzerland ............. 3188/79

[51] Int. Cl.³ .................................................. C08K 5/36
[52] U.S. Cl. .................................... 524/285; 560/51; 560/126; 560/174; 560/178; 524/289; 524/302; 524/305
[58] Field of Search ....... 260/23 A, 45.85, R, 45.85 T, 260/45.85 H; 252/406; 560/51, 126, 174, 178

[56] References Cited

U.S. PATENT DOCUMENTS

| | | | |
|---|---|---|---|
| 3,236,805 | 2/1966 | Caldo | 260/45.85 |
| 3,346,536 | 10/1967 | Kauder et al. | 260/45.85 R |
| 3,492,336 | 1/1970 | Giolite | 260/481 |
| 3,501,520 | 3/1970 | Giolito | 252/406 |
| 3,574,787 | 4/1971 | Rudolph et al. | 260/22 CA |
| 3,822,233 | 7/1974 | Stapfer | 252/406 |
| 4,057,672 | 11/1977 | Creekmore et al. | 260/23 X A |
| 4,102,839 | 7/1978 | Crochemore et al. | 260/45.85 R |

FOREIGN PATENT DOCUMENTS 1817109 12/1968 Fed. Rep. of Germany .

*Primary Examiner*—Paul R. Michl
*Attorney, Agent, or Firm*—Harry Falber

[57] ABSTRACT

Stabilizer mixtures consisting of
(a) a thioether of the formula I

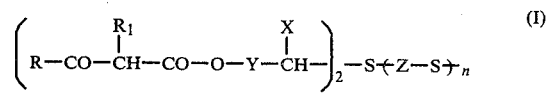

and
(b) a stabilizer containing a metal selected from the group consisting of zinc, calcium, cadmium, barium, magnesium, tin or antimony, or also zinc in combination with at least one of the metals just referred to. The definitions of the substituents and symbols in formula I will be found in claim 1.

These stabilizer mixtures ensure an excellent heat-stabilizing action in chlorinated thermoplastics.

10 Claims, No Drawings

STABILIZER MIXTURES FOR STABILIZING CHLORINATED THERMOPLASTICS

The present invention relates to new stabiliser mixtures consisting of β-ketocarboxylic acid esters of diols or polyols of thioether structure and metal-containing stabilisers for stabilising chlorinated thermoplastics, and to novel co-stabilisers of the thioether type referred to above.

A non-toxic stabiliser mixture consisting of diketoacetic acid esters and metal salts of organic acids for stabilising polyvinyl chloride resins which are intended in particular for use in food packaging, is known from German Offenlegungsschrift No. 1,569,407. It has been demonstrated, however, that this mixture does not in actual practice always lead to entirely satisfactory results as regards the stabilising action.

Surprisingly, it has now been found that mixtures of β-ketocarboxylic acid esters of diols or polyols of thioether structure and metal-containing stabilisers ensure an excellent stabilisation of chlorinated thermoplastics which satisfies the demands of practice, while at the same time affording toxicologically safe products.

Accordingly, the invention provides stabiliser mixtures consisting of (a) a thioether of the formula I

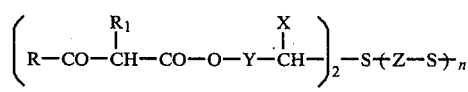

wherein n is 0 or 1, R is $C_1-C_{18}$alkyl, $C_5-C_8$cycloalkyl, $C_6-C_{10}$aryl which is unsubstituted or substituted by $C_1-C_4$alkyl, $R_1$ is hydrogen or $C_1-C_4$alkyl, X as recurrent symbol is the same or different on each recurrence and is hydrogen or a group of the formula II

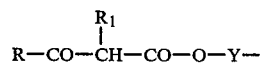

Y as recurring symbol is the same or different on each recurrence and is $C_1-C_6$alkylene or a group of the formula III

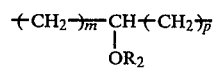

wherein the $-(CH_2)_m-$ group is bonded to the oxygen atom and $R_2$ is hydrogen or a group of the formula IV

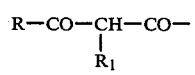

m can be an integer from 1 to 4 and p can be an integer from 0 to 3, and Z is $C_1-C_6$alkylene or a group of the formula V

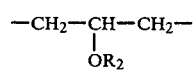

and (b) a stabiliser containing a metal selected from the group consisting of zinc, calcium, cadmium, barium, magnesium, tin (preferably monoalkyl tin) or antimony, or also and preferably zinc in combination with at least one of the above metals, especially calcium or barium.

$C_1-C_4$Alkyl can be methyl, ethyl, n-propyl, isopropyl, n-butyl, sec-butyl or tert-butyl. The preferred identity, however, is methyl.

R as $C_1-C_{18}$ alkyl is e.g. methyl, ethyl, n-propyl, isopropyl, n-butyl, sec-butyl, tert-butyl, n-pentyl, n-hexyl, n-octyl, 1,1,3,3-tetramethylbutyl, n-nonyl, decyl, dodecyl, tetradecyl, hexadecyl or octadecyl. The preferred identity of R as alkyl is $C_1-C_4$alkyl as defined above, in particular methyl.

R as $C_5-C_8$cycloalkyl can be cyclopentyl, cycloheptyl, cyclooctyl and especially cyclohexyl.

R as $C_6-C_{10}$ aryl is e.g. naphthyl or especially phenyl.

Y and Z as $C_1-C_6$alkylene are e.g. methylene, ethylene, propylene, tetramethylene, pentamethylene and hexamethylene. The preferred identities of Y and Z are methylene and ethylene.

The metal-containing stabilisers employed are Ba/Cd, Ba/Cd/Zn, organotin, preferably monoalkyl tin, and preferably Ca/Zn or Ba/Zn stabilisers, especially calcium and zinc stearate.

Especially interesting stabiliser mixtures are those containing, as component (a), a thioether of the formula I wherein n is 0 or 1, R is $C_1-C_4$alkyl, cyclohexyl, phenyl which is unsubstituted or substituted by $C_1-C_4$alkyl, $R_1$ and X are hydrogen, Y as recurring symbol is the same or different on each recurrence and is methylene, ethylene or a group of the formula III, in which the $-(CH_2)_m$ group is bonded to the oxygen atom and $R_2$ is hydrogen or a group of the formula IV, in which R and $R_1$ have the above preferred meanings, m is 1 and p is 0 or 1; and Z is methylene or ethylene.

Preferred stabiliser mixtures are those containing, as component (a), a thioether of the formula I wherein n is 0 or 1, R is methyl and $R_1$ and X are hydrogen, Y as recurring symbol is the same or different on each recurrence and is methylene or a group of the formula VI

wherein the $-CH_2-$ group is bonded to the oxygen atom and $R_2$ is hydrogen or a $CH_3-CO-CH_2-OO-$ group; and Z is methylene.

Simple compounds of the formula I, wherein n is 0 and Y is alkylene, for example the compound of the formula

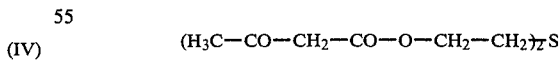

are known from Swiss Pat. No. 490,438, where they are described as booster catalysts for polyester moulding and coating compounds.

Compounds of the formula I, wherein n is 1, as well as those wherein Y is a group of the formula III, are new and constitute further embodiments of the present invention.

The thioethers of the formula I to be used in the practice of this invention are obtained very smoothly by reacting β-ketocarboxylic acid esters of the formula VII

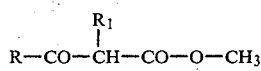

with diols or polyols of the formula VIII

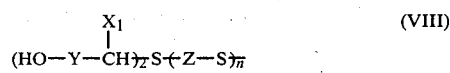

wherein $X_1$ is hydrogen or a —Y—OH group and the other symbols are as defined above.

It is advantageous to carry out this transesterification using a distillation column, as the methanol formed during the reaction can be easily separated therewith. It is desired to effect total transesterification, it is advantageous to use about twice the stoichiometric amount of methyl acetoacetate. Under stoichiometric conditions, only a partial reaction results. The reaction products, however, are also useful costabilisers. The temperature for the transesterification is in the range between 120° and 160° C. A further method of synthesis for obtaining preferred compounds of the invention comprises treating the hydroxylated thioethers of the formula VIII with diketene, e.g. in accordance with the reaction scheme:

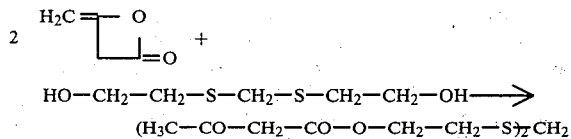

It is advantageous to use an inert solvent (e.g. toluene) as reaction medium. The concurrent use of a catalyst, e.g. pyridine, is also of advantage.

The hydroxylated thioethers or thioformals employed as starting materials for the above reactions are known per se. If some of them are new, then they can be prepared by methods analogous to known ones, e.g. by reaction of $H_2S$ or corresponding epoxide compounds, for example as follows:

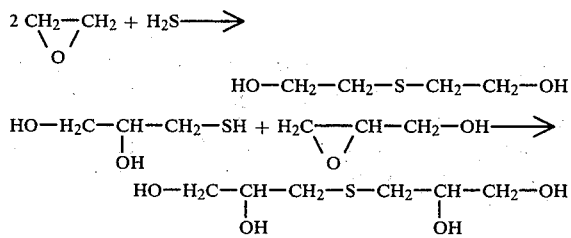

or

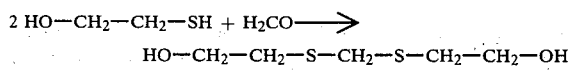

The $\beta$-ketocarboxylic acid esters of the formula VII are known compounds.

The diketene method is especially suitable for the further reaction of the thioformals to produce the compounds of the invention.

The synergistic stabiliser mixture of this invention is most suitable for protecting chlorinated thermoplastics against heat-induced degradation.

The individual components of the stabiliser mixture are incorporated in the thermoplastics to be stabilised individually or already mixed, before processing in conventional apparatus, and in respective amounts of 0.05 to 1.5% by weight, preferably 0.1 to 0.5% by weight, based on the entire composition.

Examples of chlorinated thermoplastics are polyvinylidene chloride and preferably polymers of or based on vinyl chloride. Suspension and mass polymers, and emulsion polymers having a low content of emulsifier, are preferred. Polyvinyl chloride can be plasticised or rigid PVC.

Examples of comonomers for thermoplastics based on vinyl chloride are: vinylidene chloride, trans-dichloroethane, ethylene, propylene, butylene, maleic acid, acrylic acid, fumaric acid or itaconic acid.

Depending on the end use, further additives can be incorporated in the moulding compound before, during or after the addition of the stabiliser mixture of the invention.

Examples of further additives with which the stabilisers of the invention can be used, are: antioxidants, such as 2,6-dialkylphenols, derivatives of alkylated hydroquinones, hydroxylated thiodiphenyl ethers, alkylidene bisphenols, O-, N- and S-benzyl compounds, hydroxybenzylated malonates, hydroxybenzyl aromatics, s-triazine compounds, amides of $\beta$-(3,5-di-tert-butyl-4-hydroxyphenyl)-propionic acid, esters of $\beta$-(3,5-di-tert-butyl-4-hydroxyphenyl)-propionic acid, esters of $\beta$-(5-tert-butyl-4-hydroxy-3-methylphenyl)-propionic acid, esters of $\beta$-(5-tert-butyl-4-hydroxyphenyl-acetic acid, acylaminophenols, benzylphosphonates, aminoaryl derivatives, UV absorbers and light stabilisers, such as 2-(2'-hydroxyphenyl)-benztriazoles, 2,4-bis-(2'-hydroxyphenyl)-6-alkyl s-triazines, 2-hydroxybenzophenones, 1,3-bis-2-(2'-hydroxybenzoyl)-benzenes, esters of substituted or unsubstituted benzoic acids, acrylates, nickel compounds, sterically hindered amines, oxalic acid diamides, metal deactivators, phosphites, compounds which decompose peroxide, polyamide stabilisers, basic co-stabilisers, PVC stabilisers, nucleination agents or other additives, for example plasticisers, lubricants, emulsifiers, fillers, carbon black, asbestos, kaolin, talc, glass fibres, pigments, fluorescent whitening agents, flame retardants, antistatic agents.

Examples of further additives with which the stabilisers of the present invention can be used are listed on pages 18–24 of German Offenlegungsschrift 2,427,853.

The stabiliser mixture used in the practice of this invention ensures an excellent heat-stabilising action which far exceeds that of the individual components.

The following Examples described the invention in more detail. Parts and percentages therein are by weight.

PREPARATORY EXAMPLES

Example 1

Reaction of thiodiglycerol and methyl acetoacetate 18.2 g (0.1 mole) of thiodiglycerol and 46.4 g (0.4 mole) of methyl acetoacetate are heated together to about 150° C. in a round flask equipped with a distillation head. The methanol formed during the transesterification is collected in a receiver. Non-reacted methyl acetoacetate (13.1 g) is separated off in vacuo at 60° C., affording as residue 29.7 g of a viscous yellow fluid with a refractive index of $n_D^{20}$:1.5043. The resultant product (product 1) has the formula

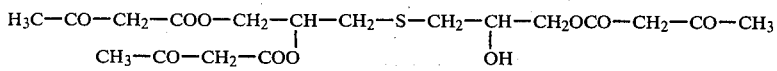

All four OH groups of the thiodiglycerol can be esterified without difficulty by reacting this latter with excess acetoacetate. On the other hand, it is also possible to obtain products containing a higher proportion of OH groups using less than stoichiometric amounts of methyl acetoacetate.

EXAMPLE 2

Reaction of thiodiglycol with methyl acetoacetate
122.2 g of bis-(2-hydroxyethyl) sulfide and 465 g of methyl acetoacetate are heated to 130° C. in a 1 liter round flask equipped with distillation column and the temperature is slowly raised to 150° C. until the bulk of the expected amount of methanol (66 g) is distilled off. After removal of the column, excess acetoacetate is distilled off and the final remnants are removed by rotary evaporation in an oil pump vacuum. The residue is a faintly yellowish oil (product 2) which can be used as co-stabiliser without further purification. The product has the formula

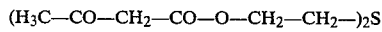

Refractive index: $n_D^{20} = 1.4889$.

EXAMPLE 3

With stirring, a mixture of 24.4 g (0.2 mole) of thiodiethylene glycol and 153 g (0.8 mole) of ethyl benzoylacetate is heated in a distillation apparatus to 160° C., in the process of which about 14 g (calculated: 19.2 g) of ethanol are distilled off. The remaining ethanol is removed in a water jet vacuum at a bath temperature of 135° C. Then excess ethyl benzoylacetate is distilled off in an oil pump vacuum. The residual product (74.4 g≃90% of theory) contains more than 95% of thiodiethylene glycol bis-benzoylacetate (product 3). Refractive index: $n_D^{20} = 1.5785$.

APPLICATION EXAMPLES

A. A dry blend consisting of 100 parts of S-PVC (K-value 58), 2 parts of epoxidised soybean oil, 0.9 part of calcium stearate, 0.6 part of zinc stearate and the amount in % (based on the total composition) of costabiliser of thioether structure indicated in Table 1 are rolled on a mixer roll for 5 minutes at 180° C. Samples having a thickness of 0.3 mm are taken from the rolled sheet obtained. The samples are subjected to heat in an oven at 180° C. and every 5 minutes the thermal ageing of a sample is determined according to the Yellowness Index (YI) of ASTM D 1925-70. The results are reported in Table I.

TABLE 1

| Test | Costabiliser | % | Rolled Sheet | Yellowness Index after 5 min. | 10 min. | 15 min. | 20 min. | 25 min. | 30 min. |
|---|---|---|---|---|---|---|---|---|---|
| 1 | — | — | 37.3 | 54.0 | 55.6 | 51.3 | 48.3 | 50.7 | black |
| 2 | product 1 | 0.2 | 15.7 | 24.0 | 31.2 | 33.4 | 44.3 | 43.2 | 80.9 |
| 3 | product 1 | 0.4 | 8.8 | 13.7 | 18.1 | 17.5 | 25.9 | 26.1 | 53.9 |
| 4 | product 2 | 0.2 | 9.3 | 14.2 | 17.4 | 18.9 | 26.9 | 30.8 | black |
| 5 | product 2 | 0.4 | 7.8 | 13.5 | 14.3 | 16.3 | 29.9 | 44.6 | " |

The rolled sheets were also pressed at 180° C. and 200 atmos. for 1 minute to 1 mm sheets and their Yellowness Index measured. The results are reported in Table 2.

TABLE 2

| Test | Costabiliser | % | Yellowness Index |
|---|---|---|---|
| 1 | — | — | 132.3 |
| 2 | product 1 | 0.2 | 73.3 |
| 3 | product 1 | 0.4 | 43.3 |
| 4 | product 2 | 0.2 | 47.8 |
| 5 | product 2 | 0.4 | 32.3 |

B. A composition suitable for the production of transparent bottles was prepared from the following ingredients:

| | | |
|---|---|---|
| suspension PVC (K-value 58) | 100 | parts |
| epoxidised soybean oil | 3 | parts |
| calcium stearate | 0.2 | part |
| zinc stearate | 0.2 | part |
| lubricant | 1.2 | parts |
| thiodiethylene glycol bis-benzoylacetate | 0.5 | part |

The dry blend, which was prepared in a fluid mixer, was rolled at 190° C. and samples of the rolled sheet obtained were taken every 5 minutes in order to determine their discolouration (Yellowness Index). The results are reported in the following table.

| Costabiliser | Yellowness Index after 5 min. | 10 min. | 15 min. | 20 min. | 25 min. | 30 min. |
|---|---|---|---|---|---|---|
| product 3 | 5.8 | 8.0 | 15.0 | 25.3 | 53.4 | 77.0 |

What is claimed is:
1. A stabilizer mixture consisting of
(a) a thioether of the formula I

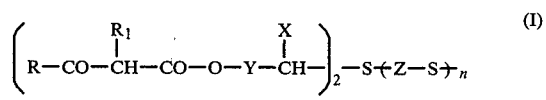

wherein n is 0 or 1, R as recurrent symbol is the same or different on each recurrence and is $C_1$–$C_{18}$alkyl, $C_5$–$C_8$ cycloalkyl, $C_6$–$C_{10}$ aryl which is unsubstituted or substituted by $C_1$–$C_4$alkyl, $R_1$ as recurrent symbol is the same or different on each recurrence and is hydrogen or $C_1$–$C_4$alkyl, X as recurrent symbol is the same or different on each recurrence and is hydrogen or a group of the formula II

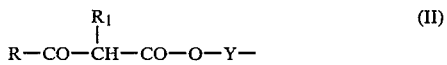

Y as recurring symbol is the same or different on each recurrence and is $C_1$–$C_6$alkylene or a group of the formula III

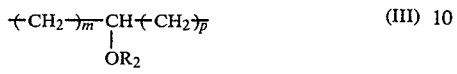

wherein the $-(CH_2)_m$ group is bonded to the oxygen atom and $R_2$ is hydrogen or a group of the formula IV

m is an integer from 1 to 4 and p is an integer from 0 to 3, and Z is $C_1$–$C_6$alkylene or a group of the formula V

wherein $R_2$ is as previously defined, and (b) a stabilizer containing a metal selected from the group consisting of zinc, calcium, cadmium, barium, magnesium, tin and antimony, or also zinc in combination with at least one of the above metals.

2. A stabiliser mixture according to claim 1 which contains, as component (a), a thioether of the formula I wherein n is 0 or 1, R is $C_1$–$C_4$alkyl, cyclohexyl, phenyl which is unsubstituted or substituted by $C_1$–$C_4$alkyl, $R_1$ and X are hydrogen, Y as recurring symbol is the same or different on each recurrence and is methylene, ethylene or a group of the formula III, in which the $-(CH_2)_m$ group is bonded to the oxygen atom and $R_2$ is hydrogen or a group of the formula IV, in which R and $R_1$ have the preferred meanings assigned to them above, m is 1 and p is 0 or 1; and Z is methylene or ethylene.

3. A stabiliser mixture according to claim 1, which contains as component (a), a thioether of the formula I wherein n is 0 or 1, R is methyl and $R_1$ and X are hydrogen, Y as recurring symbol is the same or different on each recurrence and is methylene or a group of the formula VI

wherein the $-CH_2-$ group is bonded to the oxygen atom and $R_2$ is hydrogen or a $CH_3-CO-CH_2-CO-$ group; and Z is methylene.

4. A stabiliser mixture according to claim 1, wherein component (b) is a stabiliser containing zinc in combination with calcium or barium.

5. A stabiliser mixture according to claim 1, wherein component (b) is a mixture of calcium stearate and zinc stearate.

6. A stabilised composition comprising a chlorinated thermoplastic polymer and, as stabiliser, a stabiliser mixture according to claim 1 which contains components (a) and (b) in respective amounts of 0.05 to 1.5% by weight, based on the entire composition.

7. A stabilised composition according to claim 6 which additionally contains a light stabiliser.

8. A stabilized composition according to claim 6, wherein the chlorinated thermoplastic is a homopolymer or copolymer of vinyl chloride.

9. A thioether of the formula I

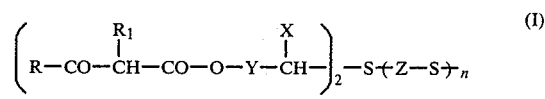

wherein n is 1, R as recurrent symbol is the same or different on each recurrence and is $C_1$–$C_{18}$alkyl, $C_5$–$C_8$cycloalkyl, $C_6$–$C_{10}$aryl which is unsubstituted or substituted by $C_1$–$C_4$alkyl, $R_1$ as recurrent symbol is the same or different on each recurrence and is hydrogen or $C_1$–$C_4$alkyl, X as recurrent symbol is the same or different on each recurrence and is hydrogen or a group of the formula II

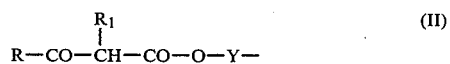

Y as recurring symbol is the same or different on each recurrence and is $C_1$–$C_6$alkylene or a group of the formula III

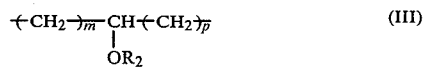

wherein the $-(CH_2)_m$ group is bonded to the oxygen atom and $R_2$ is hydrogen or a group of the formula IV

m ia an integer from 1 to 4 and p is an integer from 0 to 3, and Z is $C_1$–$C_6$alkylene or a group of the formula V

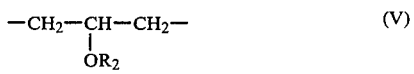

wherein $R_2$ is as previously defined.

10. A thioether of the formula I

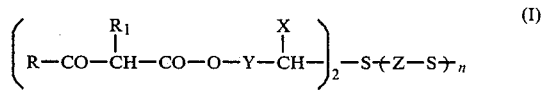

wherein n is 0 or 1, R as recurrent symbol is the same or different on each recurrence and is $C_1$–$C_{18}$alkyl, $C_5$–$C_8$cycloalkyl, $C_6$–$C_{10}$aryl which is unsubstituted or substituted by $C_1$–$C_4$alkyl, $R_1$ as recurrent symbol is the same or different on each recurrence and is hydrogen or $C_1$–$C_4$alkyl, X as recurrent symbol is the same different on each recurrence and is hydrogen or a group of the formula II

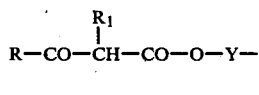 (II)
Y as recurring symbol is the same or different on each recurrence and is a group of the formula III
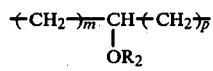 (III)
wherein the $-(CH_2)_m-$ group is bonded to the oxygen atom and $R_2$ is hydrogen or a group of the formula IV
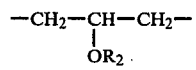 (IV)
m is an integer from 1 to 4 and p is an integer from 0 to 3 and Z is $C_1$-$C_6$ alkylene or a group of the formula V
$$-CH_2-CH-CH_2- \atop OR_2$$ (V)
wherein $R_2$ is as previously defined.
* * * * *